(12) United States Patent
Jones et al.

(10) Patent No.: US 8,444,668 B2
(45) Date of Patent: May 21, 2013

(54) EXPANDABLE VASCULAR OCCLUSION DEVICE

(75) Inventors: Donald K. Jones, Dripping Springs, TX (US); Robert R. Slazas, Miami, FL (US); Frederick Feller, III, Maple Grove, MN (US)

(73) Assignee: Depuy Synthes Products, LLC, Raynham, MA (US)

( * ) Notice: Subject to any disclaimer, the term of this patent is extended or adjusted under 35 U.S.C. 154(b) by 966 days.

(21) Appl. No.: 11/662,847

(22) PCT Filed: Sep. 16, 2005

(86) PCT No.: PCT/US2005/033398
§ 371 (c)(1),
(2), (4) Date: Mar. 14, 2007

(87) PCT Pub. No.: WO2006/034149
PCT Pub. Date: Mar. 30, 2006

(65) Prior Publication Data
US 2008/0097508 A1    Apr. 24, 2008

Related U.S. Application Data

(60) Provisional application No. 60/610,780, filed on Sep. 17, 2004.

(51) Int. Cl.
*A61M 29/00* (2006.01)
*A61B 19/00* (2006.01)

(52) U.S. Cl.
USPC .......................................... 606/200; 128/898

(58) Field of Classification Search
USPC ........................... 606/200, 191, 194; 128/898
See application file for complete search history.

(56) References Cited

U.S. PATENT DOCUMENTS

| | | | |
|---|---|---|---|
| 5,382,259 A | 1/1995 | Phelps et al. | |
| 5,395,341 A * | 3/1995 | Slater | 604/164.03 |
| 5,645,558 A | 7/1997 | Horton | |
| 5,972,019 A | 10/1999 | Engelson et al. | |
| 6,254,612 B1 | 7/2001 | Hieshima | |
| 6,361,558 B1 | 3/2002 | Heishima et al. | |
| 6,375,668 B1 * | 4/2002 | Gifford et al. | 606/200 |
| 6,551,340 B1 | 4/2003 | Konya et al. | |
| 2002/0010481 A1 | 1/2002 | Jayaraman | |
| 2003/0032976 A1 | 2/2003 | Boucek | |
| 2003/0139802 A1 | 7/2003 | Wulfman et al. | |
| 2005/0197687 A1 | 9/2005 | Molaei et al. | |
| 2006/0020286 A1 | 1/2006 | Niermann | |

OTHER PUBLICATIONS

Dieter Stoeckel, The Shape Memory Effect—Phenomenon, Alloys and Applications, NDC, 1995, pp. 1 to 13.
Canadian OA with references cited—CA2580752 dated Jul. 31, 2012.

* cited by examiner

*Primary Examiner* — Gary Jackson
*Assistant Examiner* — Michael Mendoza

(57) ABSTRACT

A vascular occlusion device that includes an inner embolic member at least partially covered by an expandable generally tubular mesh. The expandable tubular mesh typically comprises a unitary wall with apertures through the wall to assist in the expansion of the generally tubular mesh.

17 Claims, 2 Drawing Sheets

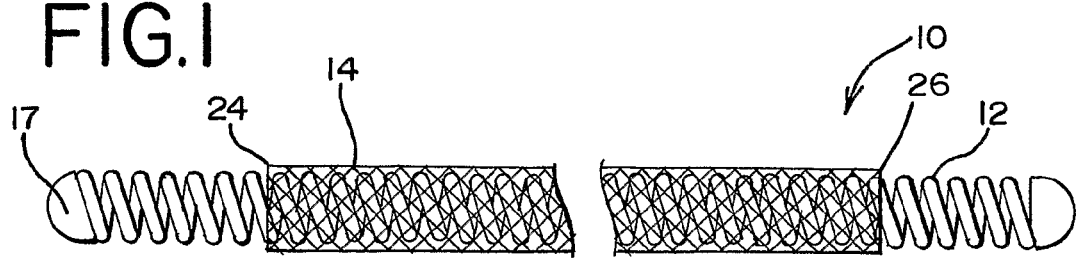
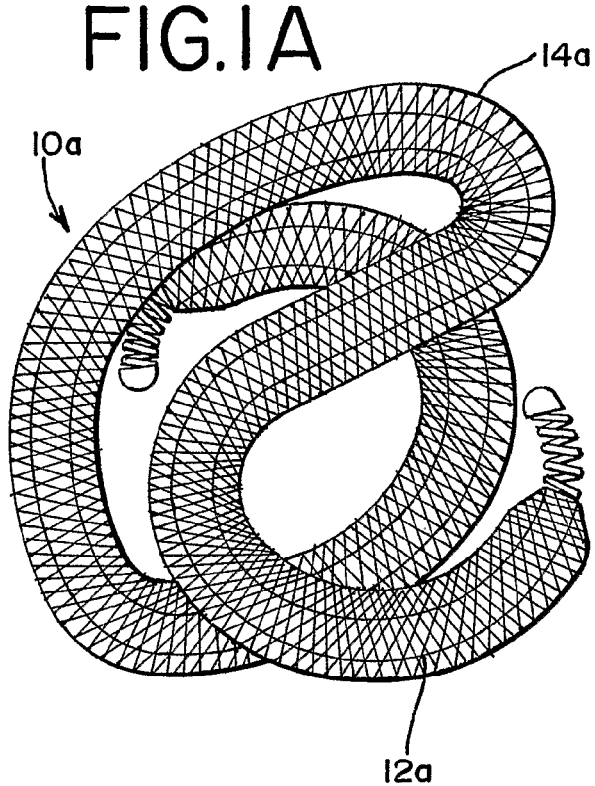
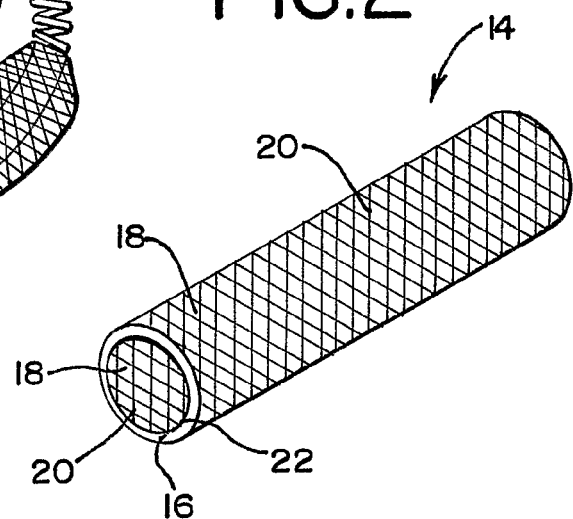
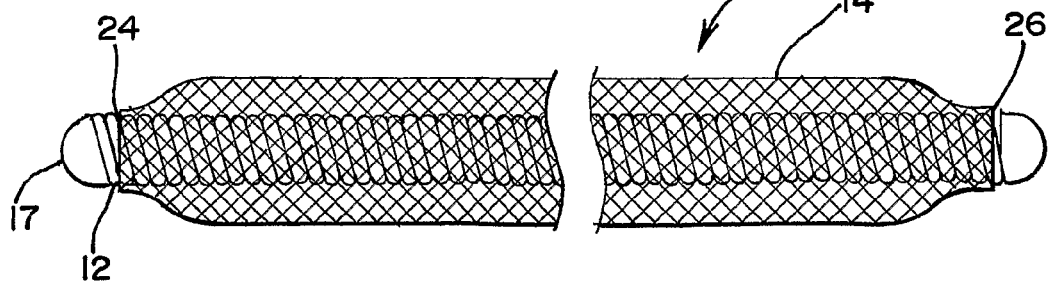

EXPANDABLE VASCULAR OCCLUSION DEVICE

This application claims priority to provisional application No. 60/610,780 filed on Sep. 17, 2004, which is hereby incorporated herein by reference.

FIELD OF THE INVENTION

The present invention generally relates to medical devices and methods which are used to occlude vessels within a patient, and more particularly, to expandable occlusion devices and methods that employ the same.

BACKGROUND OF THE INVENTION

An aneurysm is an abnormal bulge or ballooning of the wall of a blood vessel, which most commonly occurs in arterial blood vessels. Aneurysms typically form at a weakened point of a wall of a blood vessel. The force of the blood pressure against the weakened wall causes the wall to abnormally bulge or balloon outwardly. Aneurysms, particularly cranial aneurysms, are a serious medical condition because an aneurysm can apply undesired pressure to areas within the brain. Additionally, there is the possibility that the aneurysm may rupture or burst leading to serious medical complications including mortality.

When a patient is diagnosed with an unruptured aneurysm, the aneurysm is treated in an attempt to prevent the aneurysm from rupturing. Unruptured aneurysms have traditionally been treated by what is known as "clipping." Clipping requires an invasive surgical procedure wherein the surgeon makes incisions into the patient's body to access the afflicted blood vessel. Once the surgeon has accessed the aneurysm, he or she places a clip around the neck of the aneurysm to block the flow of blood into the aneurysm which prevents the aneurysm from rupturing. While clipping may be an acceptable treatment for some aneurysms, there is a considerable amount of risk involved with employing the clipping procedure to treat cranial aneurysms because such procedures require open brain surgery.

More recently, intravascular catheter techniques have been used to treat cranial aneurysms because such techniques do not require cranial or skull incisions, i.e., these techniques do not require open brain surgery. Typically, these techniques involve using a catheter to deliver embolic devices to a preselected location within the vasculature. For example, in the case of a cranial aneurysm, methods and procedure, which are well known in the art, are used for inserting the distal end of a delivery catheter into the vasculature of a patient and guiding the catheter through the vasculature to the site of the cranial aneurysm. A vascular occlusion device is then attached to the end of a pusher member which pushes the occlusion device through the catheter and out of the distal end of the catheter where the occlusion device is delivered into the aneurysm.

Once the occlusion device has been deployed within the aneurysm, the blood clots on the occlusion device and forms a thrombus. The thrombus forms an occlusion which seals off the aneurysm, preventing further ballooning or rupture. The deployment procedure is repeated until the desired number of occlusion devices are deployed within the aneurysm. Typically, it is desired to deploy enough coils to obtain a packing density of about 20% or more, preferably about 35% and more if possible.

The most common vascular occlusion device is an embolic coil. Embolic coils are typically constructed from a metal wire which has been twisted into a helical shape. One of the drawbacks of embolic coils is that they do not provide a large surface area for the blood to clot. Additionally, the embolic coil may be situated in such a way that there are relatively considerable gaps between adjacent coils in which blood may freely flow. The addition of extra coils into the aneurysm does not always solve this problem because deploying too many coils into the aneurysm may lead to an undesired rupture.

Therefore, there remains a need that is recognized and addressed according to the present invention for an occlusion device which provides a greater surface area to promote blood clotting, and also effectively occupies the space between adjacent occlusion devices without increasing the risk of rupturing the aneurysm.

SUMMARY OF THE INVENTION

The present invention generally relates to vascular occlusion devices and methods for occluding vessels within a patient. The vascular occlusion device includes an inner embolic member which is at least partially covered by a generally tubular expandable mesh. The generally tubular expandable mesh is formed from a wall having apertures extending through the wall. The device is assembled by inserting the inner embolic member into the generally tubular expandable mesh, and attaching the generally tubular expandable mesh to the inner embolic member.

The vascular occlusion device exhibits a collapsed state, wherein the generally tubular mesh is collapsed, and an expanded state, wherein the generally tubular mesh is expanded in a generally radial direction. The vascular occlusion device, in the collapsed state, may be associated with a standard delivery catheter deployment system and deployed to a preselected site within the vasculature using techniques and professional methods known in the art. Upon deployment of the vascular occlusion device at the preselected site within the vasculature of the patient, the vascular occlusion device transforms to the expanded state, and the generally tubular mesh and/or sections of the generally tubular mesh expand in a generally radial direction.

In the expanded state, the expanded generally tubular mesh occupies the space between adjoining vascular occlusion devices or between the device and tissue walls. Additionally, the expanded mesh provides for a large surface area to promote clotting of the patient's blood and assist in the occlusion effects.

Therefore, it is an object or aspect of the present invention to provide a vascular occlusion device that provides a large surface area for the promotion of blood clotting.

It is also an object or aspect of the present invention to provide a vascular occlusion device that expands to occupy a greater space within the vessel of a patient after deployment to a location requiring occlusion.

Other aspects, objects and advantages of the present invention will be understood from the following description according to the preferred embodiments of the present invention, specifically including stated and unstated combinations of the various features which are described herein, relevant information concerning which is shown in the accompanying drawing.

BRIEF DESCRIPTION OF THE DRAWINGS

In describing the preferred embodiments of the present invention, reference will be made to the accompanying drawings, wherein:

FIG. 1 is a side elevation view of an embodiment of the vascular occlusion device of the present invention in its collapsed state;

FIG. 1A is a side elevation view of an embodiment of a vascular occlusion device of the present invention which is configured to have complex curves.

FIG. 2 is a perspective view of the generally tubular element of the occlusion device of FIG. 1;

FIG. 3 is a side elevation view of another embodiment of the vascular occlusion device of the present invention in an expanded state;

DESCRIPTION OF THE PREFERRED EMBODIMENTS

Figure 4:
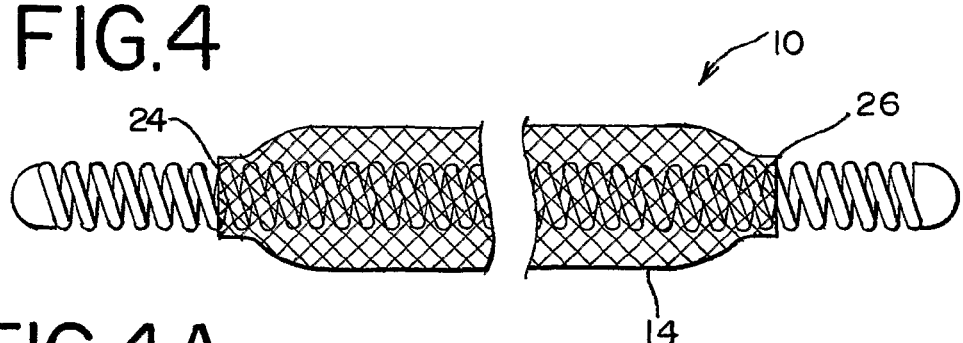
FIG. 4 is a side elevation view of the vascular occlusion device of FIG. 1 shown with the expandable generally tubular element in an expanded position.

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

The occlusion devices of the present invention are generally designed to be delivered to a preselected site within a vessel of a patient by using standard deployment systems, such as the TRUFILL® DCS ORBIT™ (Cordis Corporation) hydraulic detachable coils deployment system, other mechanical, electrolytic or thermal systems or the like, or any other deployment systems or techniques that may be developed in the future. For the sake of simplicity, the following description of the present invention will be described in terms of a vascular occlusion device. The description herein should not be considered to the limit the invention to only endovasculature procedures.

FIG. 1 generally illustrates a preferred embodiment of the vascular occlusion device 10 in the collapsed position prior to being deployed to a preselected site within the vasculature of a patient, such as an aneurysm. The vascular occlusion device 10 is comprised of an inner embolic device 12 and an expandable generally tubular element 14. The inner embolic device 12 is generally illustrated as a standard embolic coil, and alternatively, the embolic device 12 may be comprised of any of the various types of embolic devices having various shapes and configurations, such as helical coils, spheres, ellipses, spirals, complex curves and the like. For example, the device may take the form of an occlusion device 10a that includes an embolic coil 12a having complex curves wherein the generally tubular mesh 14a follows the along the curvature of the embolic coil 12a, as illustrated in FIG. 1A. Additionally, the embolic device may be constructed from a variety of different biocompatible materials, such as metals, polymers or a combination of metals and polymers.

Preferably, the inner embolic device is an embolic coil which is formed from bending a flexible wire into a helical shape. The wire preferably has a diameter of between about 0.0005 inches (about 0.013 mm) and about 0.004 inches (about 0.1 mm). The overall diameter of the coil is preferably between about 0.005 (about 0.13 mm) and about 0.015 inches (about 0.38 mm). The flexible wire is also preferably comprised of platinum or tungsten so as to provide radiopacity which aids in the delivery of the vascular occlusive device. Further, the embolic coil may include an attachment element, such as a coil head 17 which may be adapted to be attached to any of the above-identified deployment systems or others as desired.

FIG. 2 generally illustrates the expandable generally tubular element 14 which is preferably comprised of a super elastic thin film metal having shape memory, such as a nickel-titanium alloy, and more specifically a thin film of nitinol. However, the expandable generally tubular elements also may be comprised of any other metal, polymers, combination of metals and polymers or any other suitable biocompatible material. Additionally, although the generally tubular element 14 is illustrated as generally cylindrically shaped, it is contemplated that the generally tubular element could also be in the form of different shapes, for example, an elongated generally cubical shape.

The generally tubular elements are each comprised of a wall 16 which includes apertures 18 that extend through the wall. Preferably, the thickness of the wall is between about 10 microns and about 150 microns, and the total cross-sectional width of the generally tubular element, in the collapsed position, is closely larger than the cross-sectional width of the inner embolic device. When the generally tubular element is constructed from a thin film material, such as a thin film of nitinol, the thickness of the thin film is preferably between about 0.1 and 250 microns and typically between about 1 and 30 microns thick. More preferably, the thickness of the thin film is between about 1 to 10 microns and at least about 0.1 microns but less than 5 microns. In its preferred form, the generally tubular element is of unitary construction. It also can be effectively seamless.

The generally tubular element 14 may be manufactured by sputtering a metal, such as a nickel and titanium alloy, for example a nitinol, onto a cylindrical mandrel using machinery and techniques that are well known in the art. As in the embodiment illustrated in FIG. 2, apertures 18 may then be formed in the wall 16 of the generally tubular element 14 by perforating the wall by laser cutting or by any other conventional means or mechanical process. It is also contemplated that any other manufacturing process, such as molding, could be employed to fabricate the generally tubular element 14. When the generally tubular element 14 is comprised of a nitinol, the generally tubular element may be martensite, or austenite with a transition from martensite to austenite.

The apertures 18 in the generally tubular element 14 create a unitary frame work or mesh 20 in the wall 16. The apertures 18 may be of any size and shape, and may be uniformly or randomly spaced throughout the wall 16 of the generally tubular element 14. The apertures 18 provide the tubular element with flexibility and also assist in the transformation of the generally tubular element from the collapsed state to the expanded state, and vice versa.

To assemble the vascular occlusion device 10, the inner embolic member 12 is inserted into the opening 22 located at either end of the generally tubular element 14 so that the mesh 20 of the generally tubular element covers at least a portion of the inner embolic device 12. As illustrated in FIG. 3, an alternative embodiment, the generally tubular element 14 may cover substantially the entire inner embolic device 12, leaving at least one end, i.e., the coil head 17, uncovered for attachment to a deployment system. The generally tubular element 14 is then attached (not shown) to the inner embolic member 12 by biocompatible adhesives, solder, welding, or other approach suitable for use in the body. In the embodiments illustrated in FIGS. 1 through 6, the generally tubular element 14, 14a, 14b is attached to the inner embolic device 12, 12a, 12b at the proximal end 24 and distal end 26 (as shown in FIG. 1) of the generally tubular element. It is contemplated that the generally tubular element could be connected to the inner embolic device in any number of places.

FIG. 4 illustrates one embodiment of the vascular occlusion device 10 in the expanded position. In the expanded position, the generally tubular element is uniformly expanded in a generally radial direction. The expanded diameter of the generally tubular element may range from about 0.003 inches (about 0.08 mm) to about 0.250 inches (about 6.35 mm), with a preferred range for neurovascular applications from about 0.008 inches (about 0.2 mm) to about 0.025 inches (about 0.64 mm). Less expansion may be exhibited when expansion is limited by available space at the deployment site.

Figure 4A:
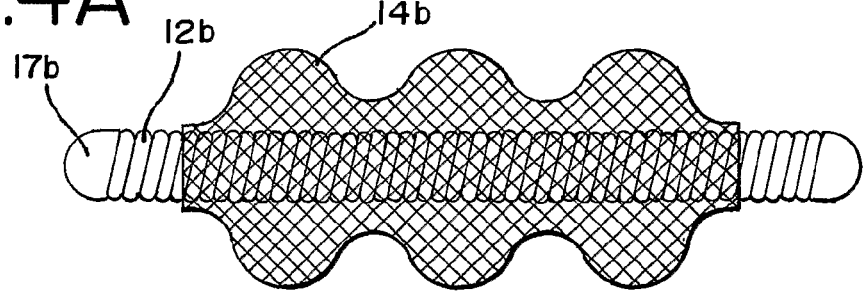
FIG. 4A is a side elevation view of another embodiment of a vascular occlusion device of the present invention shown in an alternative expanded shape.

In the expanded state, the tubular mesh element may also have different configurations and shapes. For example, as illustrated in FIG. 4A, in the expanded state, the outer surface of the tubular mesh element 14b may have a curved configuration. This curved configuration may be obtained by heat treating the tubular mesh element in a mold having a shape corresponding to that of illustrated tubular mesh element 14b. It will be understood that different shaped molds will yield different configurations for the expanded tubular element.

The transformation of the generally tubular element may be activated by different methods. For example, the wall of the delivery catheter may contain the vascular occlusion device in the collapsed position until the vascular occlusion device is deployed from the distal end of the delivery catheter. Once free from the containment of the catheter wall, the vascular occlusion device is allowed to expand. Alternatively, when the generally tubular element is comprised of a shape memory material, such as a nitinol, the transformation from the collapsed state to the expanded stated could be temperature activated. In one preferred embodiment, the transformation of the generally tubular element is activated at body temperature.

Figure 5:
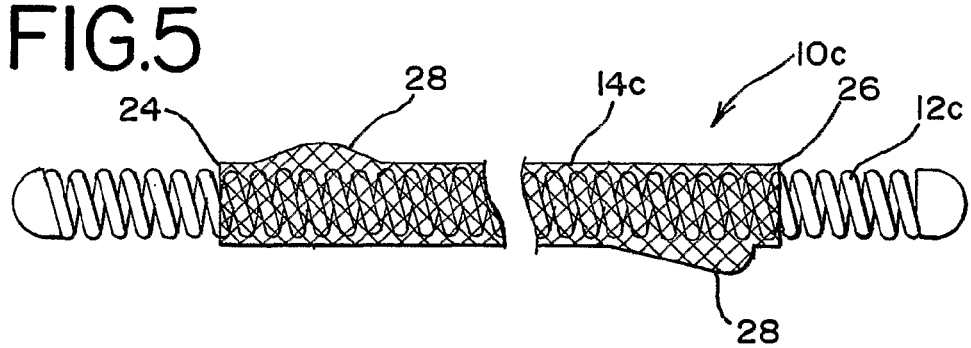
FIG. 5 is side elevation view of an occlusion device of the present invention shown with the expandable generally tubular element in a partially expanded position.

In another embodiment, a vascular occlusion device 10c includes a generally tubular element 14c comprised of a material which is not self expanding. As illustrated in FIG. 5, the generally tubular element 14c includes sections 28 which are expanded in a generally radial direction. The sections 28 can be formed from pressure exerted by the inner embolic device 12c against the generally tubular element 14c. For example, as the vascular occlusive device 10c is packed into an aneurysm, the inner embolic device 12c bends and flexes while being maneuvered into the aneurysm and between adjacent occlusive devices. When the inner embolic device 12c bends, it presses against the wall 16 of the generally tubular element 14c expanding sections 28 outwardly in a generally radial direction. Thus, the generally tubular element 14c may include non-uniform expanded sections. The sections 28 are illustrative of this concept and are not intended to illustrate all possibilities for partial expansion of the generally tubular element. The generally tubular element 14b may be formed from many metals or polymers not exhibiting shape memory properties including platinum, tungsten, stainless steel, nylon and polyethylene. In addition, the generally tubular element may comprise shape memory materials such as nitinol, where the nitinol remains in the martensitic state.

In addition to the features described herein, the vascular occlusion device, i.e., the inner embolic device and the generally tubular element, may also include one or more bioactive materials, such as fibrous materials, foam materials, coatings, therapeutic agents, thrombogenic agents, non-thrombogenic agents, growth factors and the like.

Figure 6:
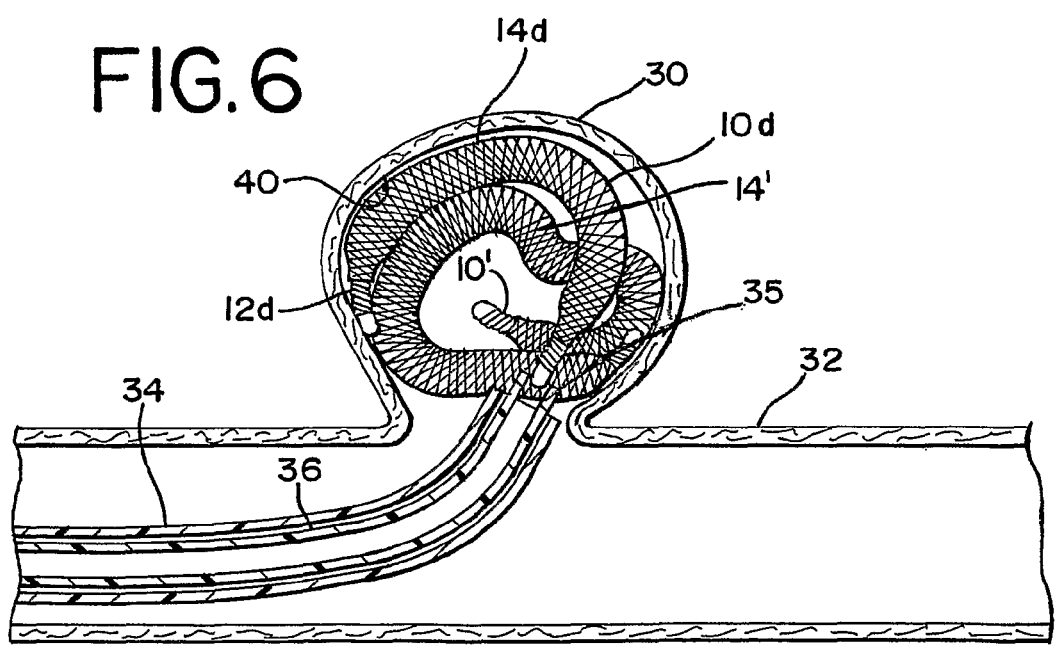
FIG. 6 is schematic illustration showing multiple vascular occlusion devices of the invention deployed within an aneurysm.

The occlusion devices described herein are designed to be deployed to a preselected site within a vessel of the body. FIG. 6 is a schematic illustration showing the treatment of an aneurysm 30 of a blood vessel 32. A delivery catheter 34 is guided through the vascular system to the site of an aneurysm 30 using standard techniques and professional methods known in the art. The collapsed vascular occlusion device 10d is releasably attached to the distal end 35 of a pusher 36 which pushes and guides the vascular occlusion device 10d through the delivery catheter 34 to the site of the aneurysm 30. The vascular occlusion device 10d is guided out of the distal end 38 of the delivery catheter 34 into the aneurysm 30, where it is released from the distal end 35 of the pusher 36. The generally tubular element 14d of the vascular occlusion device 10d expands either by the nature of the material or by force of the inner embolic device 12d against the wall tubular element, as describe above. The expanded generally tubular element 14d increases the amount of space the vascular occlusion device 10d occupies and increases the surface area onto which the blood can clot and form a thrombus.

As also illustrated in FIG. 6, the expanded generally tubular element 14d, in the expanded position, preferably is flexible and elastic so that the generally tubular element 14d may yield to pressure from surrounding vascular occlusion devices, such as 10', and/or the wall 40 of the vessel 32. The flexible and elastic characteristics of the generally tubular elements 14d and 14' allow the generally tubular elements to fill in the space between adjacent vascular occlusion devices 10d and 10' without creating a high-pressure situation, and thus reducing the risk of a rupture.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. An occlusion device comprising:
a generally tubular element which is capable of being transformed between a collapsed position and an expanded position, said tubular element being formed by a wall having a plurality of apertures extending through the wall;
an inner embolic device located at least partially within the generally tubular element so that at least a portion of the inner embolic device is covered by the expandable generally tubular element; and
said expandable generally tubular element is attached to the inner embolic device, wherein the tubular element has a preselected shape in the expanded position;
wherein the generally tubular element expands at body temperature.

2. The occlusion device of claim 1 wherein the generally tubular element covers substantially the entire inner embolic device.

3. The occlusion device of claim 1 wherein the generally tubular element further includes a proximal end and a distal end, and at least the proximal end and the distal end are attached to the inner embolic member.

4. The occlusion device of claim 1 wherein the generally tubular element comprises a material having super-elastic properties.

5. The occlusion device of claim 1 wherein the generally tubular element comprise a material having shape memory.

6. The occlusion device of claim 1 wherein the generally tubular element comprises a metal.

7. The occlusion device of claim 6 wherein the metal is a nickel-titanium alloy.

8. The occlusion device of claim 1 wherein the inner embolic device is an embolic coil.

9. The occlusion device of claim 1 wherein the embolic coil is configured to have complex curves.

10. The occlusion device of claim 1 wherein the apertures are formed by perforating the wall.

11. The occlusion device of claim 1 wherein the tubular element wall is unitary and at least a portion of the generally tubular element expands in response to pressure applied by the inner embolic device.

12. An intraluminal device, comprising:
an embolic coil; and
an expandable generally tubular thin film mesh covering at least a portion of the embolic coil and being attached to the embolic coil, said generally tubular thin film mesh comprising a perforated unitary wall, wherein the tubular thin film mesh has a preselected shape in an expanded position;
wherein the generally tubular thin film mesh expands at body temperature.

13. The intraluminal device of claim 12 wherein the expandable generally tubular thin film mesh covers substantially the entire embolic coil.

14. The intraluminal device of claim 12 wherein the expandable generally tubular thin film mesh includes a proximal end and a distal end wherein at least the proximal end and the distal end are attached to the embolic coil.

15. The intraluminal device of claim 12 wherein the expandable generally tubular thin film mesh has a thickness greater than about 0.1 microns but less than about 5 microns.

16. A method of occluding a vessel within a patient, comprising:
using an occlusion device having a generally tubular element which is capable of being transformed between a collapsed position and an expanded position, the tubular element has a preselected shape in the expanded position, said tubular element being formed by a wall having a plurality of apertures extending through the wall, and an inner embolic device at least partially within the generally tubular element so that at least a portion of the inner embolic device is covered by the expandable generally tubular element, said expandable generally tubular element being attached to the embolic device;
placing the vascular occlusion device within a vessel of a patient and directing same to a diseased-location of the vessel; and
expanding the generally tubular element at body temperature in the diseased location.

17. The method according to claim 16 wherein the providing further includes providing a generally tubular element that expands upon a rise in temperature; and
the expanding comprises raising the temperature of the generally tubular element.

\* \* \* \* \*